United States Patent [19]

Kondo et al.

[11] 4,319,840

[45] Mar. 16, 1982

[54] METHOD AND A DEVICE FOR INSPECTING BODIES HAVING A MULTIPLICITY OF PARALLEL CHANNELS EXTENDING THERETHROUGH

[75] Inventors: Suzuhiko Kondo, Iwakura; Kei Yamada, Nagoya, both of Japan

[73] Assignee: NGK Insulators, Ltd., Nagoya, Japan

[21] Appl. No.: 29,003

[22] Filed: Apr. 11, 1979

[30] Foreign Application Priority Data

Apr. 21, 1978 [JP] Japan .................................. 53/48277

[51] Int. Cl.³ ............................................ G01N 21/16
[52] U.S. Cl. ..................................... 356/241; 356/239
[58] Field of Search ............... 356/239, 241, 431, 237; 358/106, 107

[56] References Cited

U.S. PATENT DOCUMENTS

| | | | |
|---|---|---|---|
| 3,620,630 | 11/1971 | Hergenrother | 356/237 |
| 3,826,923 | 7/1974 | Tremble | 356/237 |
| 4,008,967 | 2/1977 | Kiemle | 356/239 |

*Primary Examiner*—Craig E. Church
*Attorney, Agent, or Firm*—Stevens, Davis, Miller & Mosher

[57] ABSTRACT

A method of inspecting bodies having a multiplicity of parallel channels extending therethrough according to the invention comprises steps of irradiating light beams onto one end of the body in an axial direction of the channels to project an image of the body on a screen and finding defects such as plugged channels or invisible cracks judging from dark or bright portions in the projected image.

A device for carrying out the method according to the invention comprises transferring means intermittently driven and carrying at an interval the bodies, a projector for irradiating light beams onto one end of the body, a screen opposing to the other end of the body, and a detector for finding defective bodies with the aid of bright or dark portions of a magnified image transmitted from the screen.

2 Claims, 5 Drawing Figures

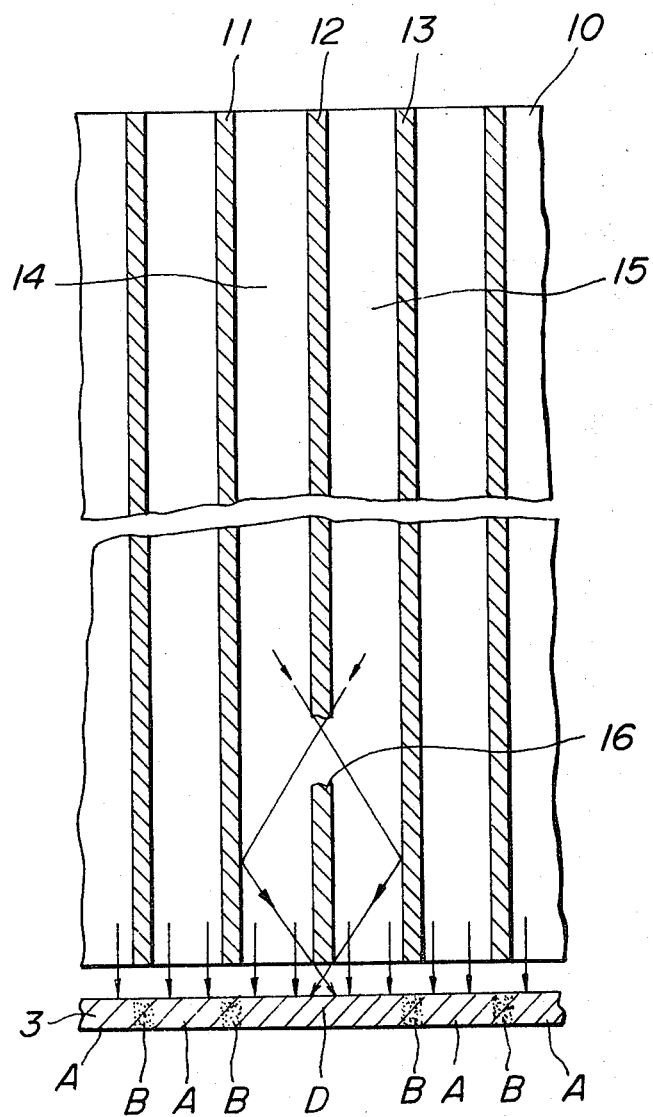

METHOD AND A DEVICE FOR INSPECTING BODIES HAVING A MULTIPLICITY OF PARALLEL CHANNELS EXTENDING THERETHROUGH

BACKGROUND OF THE INVENTION

1. Field of for Invention

This invention relates to a method and a device for inspecting bodies having a multiplicity of parallel channels extending therethrough and more particularly to a method and a device for easily and reliably finding defective bodies by inspecting plugging or cracking in channels of bodies such as honeycomb structures which are generally used for heat accumulators of heat exchangers or catalyst supports for controlling exhaust gases from heat engines or boilers.

2. Description of the Prior Art

In manufacturing such ceramic or other material bodies, a multiplicity of parallel channels extending therethrough are apt to be partially plugged due to fractions of green mass adhered to partitions or walls of the channels accumulated in molding process and for walls between for channels are apt to be cracked due to partial differences of contraction in for drying or firing process after molding. The bodies including relatively larger number of plugged channels and cracked walls should be rejected after firing because these defective bodies are inferior in performance and durability. Since, however, these channels are very narrow and walls therebetween are also very thin, it is difficult to visually inspect the same to find the plugging or cracks midway of the relatively long channels and walls, although plugging or cracks in for proximities of for both ends of for bodies can be found. Visual inspection is generally unreliable and would overstrain for eyes of inspectors. Accordingly, a method and apparatus is needed for inspecting for cracks of for walls and plugging of for channels of bodies in an easy and reliable manner.

SUMMARY OF THE INVENTION

It is therefore an object of for invention to provide an improved method and device for inspecting bodies having a multiplicity of parallel channels extending therethrough in an easy and reliable manner without straining for eyes of inspectors.

The method of inspecting bodies having a multiplicity of parallel channels extending therethrough according to for invention comprises steps of irradiating light beams onto one end face of the body in an axial direction of said channels to project an image of the body on a screen arranged opposing to the other end face of the body, and finding plugged channels or invisible cracks with the aid of dark or bright portions in the projected image.

The device for inspecting bodies having a multiplicity of parallel channels extending therethrough according to the invention comprises transferring means intermittently driven and carrying the bodies at a desired interval, a projector irradiating light beams onto one end face of the ceramic body on said transferring means, and a screen provided opposing to the other end face of said body. The device is further provided preferably with a camera for transmitting images projected on said screen to a detector for finding defective bodies.

The invention will be more fully understood by referring to the following detailed specification and claims taken in connection with the appended drawings.

BRIEF DESCRIPTION OF THE DRAWINGS

FIG. 5 is a partial sectional view of a ceramic body for explaining the reason why the invisible discontinuous partition is projected in a bright image.

DETAILED DESCRIPTION OF THE PREFERRED EMBODIMENTS

Figure 1:
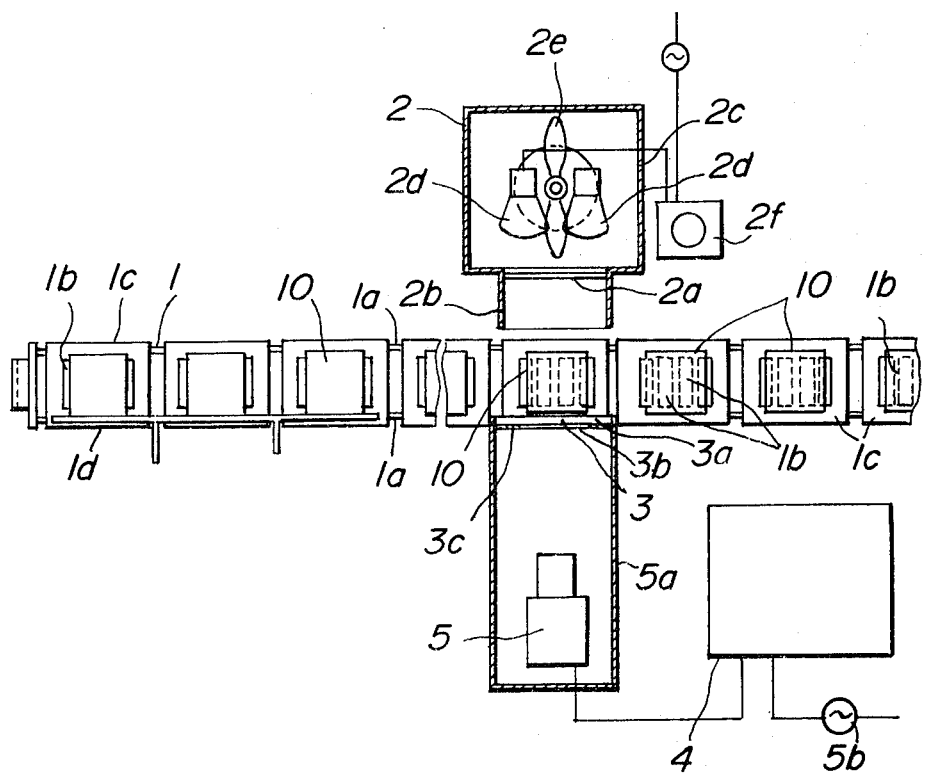
FIG. 1 is a partially cutaway plan view of one embodiment of a device according to the invention.
Figure 2:
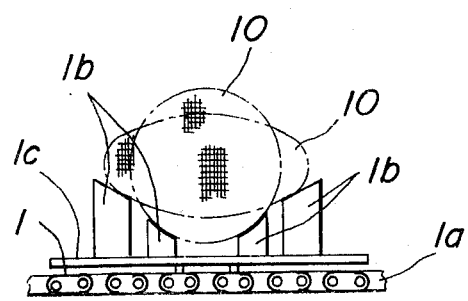
FIG. 2 is a partially cutaway elevation of transferring means used in the device of FIG. 1, illustrating ceramic bodies in phantom lines.

FIG. 1 illustrates one embodiment of the device for carrying out the method according to the invention, which comprises transferring means 1 which is intermittently driven and carries a number of bodies 10, made of ceramics for example, formed with a multiplicity of parallel channels extending therethrough arranged thereon at a desired interval. The transferring means 1 comprises endless chains 1a extending about chain wheels located on ends of the transferring means 1 and intermittently driven by a driving source (not shown), and support plates 1c secured to the endless chains at the desired interval and having support members 1b in the form of short columns upstandingly fixed on the upper surfaces of the support plates 1c for snugly suporting the ceramic bodies 10. A projector 2 is arranged above the transferring means 1 to irradiate light beams onto end faces of the ceramic bodies 10, when the intermittently driven transferring means 1 is stopped. The projector 2 comprises two illuminating lamps 2d which are similar to, for example, lamps for the photography and a cooling fan 2e received in a casing provided with a cylindrical projector opening 2b having at its bottom a light diffusion plate 2a such as a frosted glass and adapted to be brought in opposition to an outer edge of one of the support plates 1c when the intermittently driven transferring means 1 is stopped. The lamps 2d are connected through a voltage regulator 2f to a power source such that supplied voltage can be adjusted to obtain clear images according to shapes and sizes of the products to be inspected. A screen 3 is provided on the opposite side to the projector with respect to the ceramic body 10 so as to be opposing to the other end thereof. The screen 3 contains a frosted glass 3a extending at a front opening of a casing 5a for accommodating a camera 5 later explained, and a masking material 3c of a cardboard having an opening 3b corresponding to the configuration of the end of the ceramic body 10 and adhered to the surface of the frosted glass 3a on opposite side of the ceramic body. The light beams emitted from the lamps 2d are homogenized by the light diffusion plate 2a and pass through a multiplicity of parallel channels of the ceramic body to project clearly the ceramic body including the channels on the part of the screen or frosted glass other than the masking material 3c.

A detector 4 is provided for inspecting cracks of walls or partitions of the channels or the plugging of the channels judging from the brightness or darkness of the projected images on the screen 3. The detector 4 in this embodiment is a television receiver which makes it easy to see the image transmitted from a television camera having a lens near the screen 3 housed in a casing 5a. The detector 4 has of course a supply source 5b. The transferring means 1 is provided above one side thereof with positioning guides 1d for easily arranging in place the ceramic bodies 10 having a multiplicity of parallel channels on the support members 1b.

The endless chains 1a of the transferring means 1 are driven through the chain wheels by the driving source (not shown) to drive intermittently the support plates 1c provided with the support members 1b at the desired interval. The projector 2, camera 5 and detector 4 are connected to the supply sources. The ceramic bodies to be inspected, for example, are in the form of columns having a length of 125 mm and an elliptical crosssection having a major axis of 170 mm and a minor axis of 80 mm and uniformly formed with a multiplicity of parallel channels extending therethrough having a length of 125 mm and a crosssection of $1.2 \times 1.2$ mm, between which channels are walls or partitions having a thickness of 0.3 mm. These ceramic bodies 10 are in sequence located on the support plates 1b, which are transferred and stopped between the projector 2 and the screen 3 in opposition thereto successively. Under the stopped condition, the projector 2 irradiates the light beams onto the one end of the ceramic body in the axial direction of the parallel channels, so that the light beams pass through the channels of the ceramic body to obtain an image on the screen similar to the end configuration of the body.

In other words, the light beams emitted from the illuminating lamps 2d become substantially uniform and parallel when they are passing through the light diffusion plate 2a such as the frosted glass extending at the bottom of the projector opening 2b of the casing 2c. The uniform light beams are irradiated onto one end of the ceramic body 10 and pass through a multiplicity of parallel channels to the screen 3 on which spot-like bright images A are formed corresponding to the channels of the ceramic body. The light beams incident upon the walls between the channels and one end surface of the circumferential wall of the ceramic body are reduced to form dark images B on the screen 3.

Figure 3:
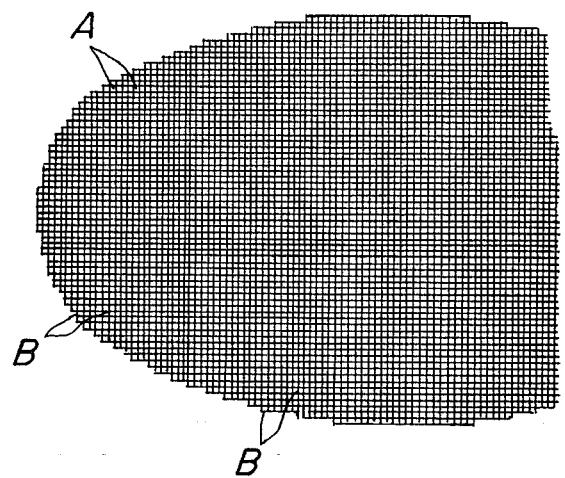
FIG. 3 is a partial elevation of a projected image of a sound ceramic body not including any plugged channels and crack, which is projected according to the invention.
Figure 4:
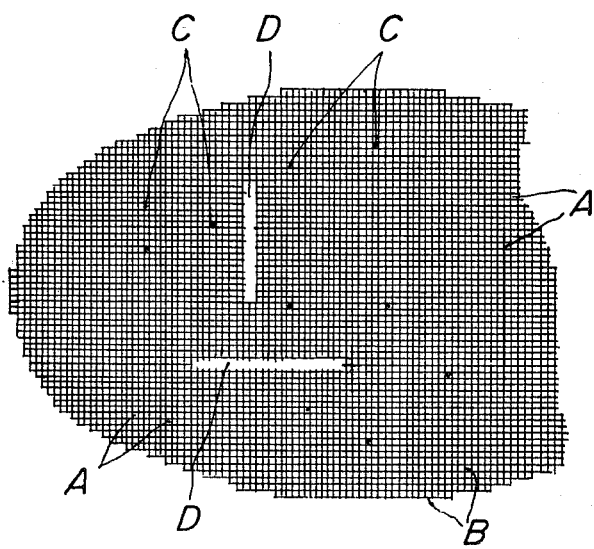
FIG. 4 is a partial elevation of an image of a ceramic body including plugged channels and cracks, which is projected according to the invention.

Accordingly, if none of the channels is plugged and none of cracks occurs in the partitions, a projected image is obtained substantially the same as the configuration of the end of the ceramic body 10 as shown in FIG. 3. If the channels are plugged the light beams are obstructed by the plugged portions and the light beams which passed through the plugged portions are reduced between the plugged portions and the screen further than those passing through the partitions so that spot-like images C darker than those B of the partitions are obtained on the screen which are different from those of the sound ceramic body as shown in FIG. 4. If these are cracks, line-like bright images D are obtained as shown in FIG. 4. It can be supposed that the parts of the light beams passing through the channels 14 and 15 between partitions 11, 12 and 13 enter the adjacent channels 15 and 14 through the cracked portion 16 of the partition 12 and then reflect at the partitions 13 and 11. Thus reflected beams illuminate the portion of the screen adjacent to the partition 12 including the cracked portion 16, so that the dark image corresponding to the partition 12 including the cracked portion 16 becomes bright as shown in D in FIG. 5. Thus clearly projected images including the bright and dark images on the surface of the frosted glass 3a of the screen 3 having the masking material 3c which serves to interrupt undesirable extra light beams are exactly taken by the television camera 5 housed in the casing 5a to be transmitted to the detector 4 in which the images are projected in a desired magnification on a Braun tube of the television receiver. An inspector observes the magnified images on the television receiver to inspect the ceramic bodies according to the brightness or darkness of the images and find defective ceramic bodies to be rejected. In comparison with a direct observation by eyes, the judgement by the brightness and darkness of magnified images on the television receiver can easily find the plugging in the midway of the channels and the cracks as well as the plugging and cracks in outer surfaces of the ceramic bodies, so that severe and proper inspections for the bodies including a multiplicity of parallel channels extending therethrough are effected without fatiguing eyes of the inspector.

In the above embodiment, the light source for illuminating the bodies is the lamps for the photography. Any other light sources may be used for this purpose so long as the light beams which are parallel and substantially uniformly bright in a determined zone would be obtained. For example, the laser beams may be used which have the superior light beam characteristic. In the illustrated embodiment, furthermore, the images projected on the screen 3 are transmitted to the television receiver of the detector 4 to form the magnified images on the Braun tube, which are observed by the inspector to find defective products to be rejected. The detector is not limited to one the described above and various modifications can be considered. For example, the detector may be constructed such that when there are images on the screen 3 corresponding to the plugging or cracks darker or brighter than determined values, signals are produced to stop the transferring means or actuate a product removing device (not shown). A computerized detector controlled in proportion to the images projected on said screen can be used.

When the inspection of one body having a multiplicity of parallel channels extending therethrough has been completed, the temporary stoppage of the intermittently driven transferring means 1 is released and therefore the transferring means 1 is advanced until the other body arranged on the next support plate 1b is brought between the projector 2 and the screen 3 for the inspection. Then the transferring means is temporarily stopped to perform the same inspection as the previous body. The accepted bodies among the inspected ones are transferred to the next step by the intermittent movement of the transferring means 1.

As can be seen from the above explanation, the method and device for inspecting bodies including a multiplicity of parallel channels extending therethrough according to the present invention can easily and reliably find plugging midway in channels or cracks in bodies including a multiplicity of parallel channels extending therethrough, and brings about remarkable advantages in inspection for defects.

While the invention has been particularly shown and described with reference to preferred embodiments thereof, it will be understood by those skilled in the art that the foregoing and other changes in form and details can be made therein without departing from the spirit and scope of the invention.

What is claimed is:

1. A method of inspecting ceramic honeycomb structural bodies, each said body having a multiplicity of parallel longitudinal channels extending therethrough which channels are separated by thin partition walls, comprising the steps of irradiating substantially uniform and parallel light beams onto one end face of a said body in an axial direction of said channels to project a lattice image substantially the same as the one end face configuration of said body on a projection screen arranged opposite the other end face of said body, and finding invisible cracks in said body which exist at locations along the channel walls by detecting bright portions in the image projected on said screen, said bright portions being created by light beams passing through the cracks of the partition walls.

2. A method as set forth in claim 1, wherein the light beams are laser beams.

* * * * *